(12) United States Patent
Gabbay (10) Patent No.: US 7,296,690 B2
(45) Date of Patent: *Nov. 20, 2007

(54) METHOD AND DEVICE FOR INACTIVATING VIRUSES

(75) Inventor: Jeffrey Gabbay, Jerusalem (IL)

(73) Assignee: The Cupron Corporation, New York City, NY (US)

( * ) Notice: Subject to any disclaimer, the term of this patent is extended or adjusted under 35 U.S.C. 154(b) by 478 days.

This patent is subject to a terminal disclaimer.

(21) Appl. No.: 10/339,886

(22) Filed: Jan. 10, 2003

(65) Prior Publication Data

US 2003/0198945 A1    Oct. 23, 2003

Related U.S. Application Data

(63) Continuation-in-part of application No. 10/133,691, filed on Apr. 24, 2002, now abandoned.

(30) Foreign Application Priority Data

Apr. 18, 2002   (IL)   ..................... 149206

(51) Int. Cl.
  *B01D 24/02*     (2006.01)
  *A01N 59/20*     (2006.01)
  *C23C 20/04*     (2006.01)
  *B01D 24/00*     (2006.01)

(52) U.S. Cl. .............. 210/501; 210/503; 210/504; 210/505; 210/508; 210/509; 424/630; 106/126

(58) Field of Classification Search .............. None
See application file for complete search history.

(56) References Cited

U.S. PATENT DOCUMENTS

| 252,524 | A | 1/1882 | Sagendorf |
| 1,210,375 | A | 12/1916 | Decker |
| 3,014,818 | A | 12/1961 | Campbell |
| 3,308,488 | A | 3/1967 | Schoonman |
| 3,385,915 | A | 5/1968 | Hamling |
| 3,663,182 | A | 5/1972 | Hamling |
| 3,769,060 | A | 10/1973 | Ida et al. |
| 3,821,163 | A | 6/1974 | Spivack |
| 3,860,529 | A | 1/1975 | Hamling |

(Continued)

FOREIGN PATENT DOCUMENTS

DE    4403016 A1    8/1995

(Continued)

OTHER PUBLICATIONS

"Encyclopedia of Polymer Science and Technology," John Wiley & Sons, Inc., (1968) vol. 8, pp. 651-666 and vol. 9, pp. 580-598.

(Continued)

*Primary Examiner*—Krishnan S. Menon
(74) *Attorney, Agent, or Firm*—Townsend and Townsend and Crew LLP (57) ABSTRACT

The invention provides a device for the inactivation of a virus comprising a housing delimiting a fluid passageway, the passageway being provided with a filtering material having ionic copper selected from the group consisting of $Cu^+$ and $Cu^{++}$ ions and combinations thereof incorporated therein.

15 Claims, 7 Drawing Sheets

U.S. PATENT DOCUMENTS

| | | | |
|---|---|---|---|
| 4,072,784 A | 2/1978 | Cirino et al. | |
| 4,103,450 A | 8/1978 | Whitcomb | |
| 4,115,422 A | 9/1978 | Welch et al. | |
| 4,174,418 A | 11/1979 | Welch et al. | |
| 4,201,825 A | 5/1980 | Ebneth | |
| 4,219,602 A | 8/1980 | Conklin | |
| 4,278,435 A | 7/1981 | Ebneth | |
| 4,291,086 A | 9/1981 | Auten | |
| 4,292,882 A | 10/1981 | Clausen | |
| 4,297,117 A * | 10/1981 | Holter et al. | 96/153 |
| 4,317,856 A | 3/1982 | Huthelker et al. | |
| 4,366,202 A | 12/1982 | Borovsky | |
| 4,390,585 A | 6/1983 | Holden | |
| 4,525,410 A | 6/1985 | Hagiwara | |
| 4,666,940 A | 5/1987 | Bischoff et al. | |
| 4,675,014 A | 6/1987 | Sustmann et al. | |
| 4,688,567 A * | 8/1987 | Kikuchi et al. | 128/206.15 |
| 4,710,184 A | 12/1987 | Ehret | |
| 4,769,275 A | 9/1988 | Inagaki et al. | |
| 4,853,019 A | 8/1989 | White et al. | |
| 4,900,618 A | 2/1990 | O'Connor et al. | |
| 4,900,765 A | 2/1990 | Murabayashi et al. | |
| 4,983,573 A | 1/1991 | Bolt et al. | |
| 4,999,240 A | 3/1991 | Brotz | |
| 5,009,946 A | 4/1991 | Hatomoto et al. | |
| 5,017,420 A | 5/1991 | Marikar et al. | |
| 5,024,875 A | 6/1991 | Hill et al. | |
| 5,066,538 A | 11/1991 | Huykman | |
| 5,143,769 A | 9/1992 | Moriya et al. | |
| 5,175,040 A | 12/1992 | Harpell et al. | |
| 5,200,256 A | 4/1993 | Dunbar | |
| 5,217,626 A | 6/1993 | Yahya et al. | |
| 5,227,365 A | 7/1993 | Van Den Sype | |
| 5,254,134 A | 10/1993 | Zhao et al. | |
| 5,269,973 A | 12/1993 | Takahashi et al. | |
| 5,316,837 A | 5/1994 | Cohen | |
| 5,316,846 A | 5/1994 | Pinsky et al. | |
| 5,370,934 A | 12/1994 | Burch et al. | |
| 5,399,425 A | 3/1995 | Burch | |
| 5,405,644 A | 4/1995 | Ohsumi et al. | |
| 5,407,743 A | 4/1995 | Clough et al. | |
| 5,411,795 A | 5/1995 | Silverman | |
| 5,458,906 A | 10/1995 | Liang | |
| 5,492,882 A | 2/1996 | Doughty et al. | |
| 5,518,812 A | 5/1996 | Mitchnick et al. | |
| 5,547,610 A | 8/1996 | Mortenson | |
| 5,549,972 A | 8/1996 | Hsu et al. | |
| 5,744,222 A | 4/1998 | Sugihara | |
| 5,848,592 A | 12/1998 | Sibley | |
| 5,849,235 A | 12/1998 | Sassa et al. | |
| 5,856,248 A | 1/1999 | Weinberg | |
| 5,869,412 A | 2/1999 | Yenni, Jr. et al. | |
| 5,871,816 A | 2/1999 | Tal | |
| 5,881,353 A | 3/1999 | Kamigata et al. | |
| 5,904,854 A | 5/1999 | Shmidt et al. | |
| 5,939,340 A | 8/1999 | Gabbay | |
| 5,981,066 A | 11/1999 | Gabbay | |
| 6,013,275 A | 1/2000 | Konagaya et al. | |
| 6,124,221 A | 9/2000 | Gabbay | |
| 6,383,273 B1 | 5/2002 | Kepner et al. | |
| 6,394,281 B2 | 5/2002 | Ritland et al. | |
| 6,482,424 B1 | 11/2002 | Gabbay | |
| 6,681,765 B2 * | 1/2004 | Wen | 128/201.25 |
| 2001/0052487 A1 * | 12/2001 | King | 210/169 |
| 2003/0196966 A1 * | 10/2003 | Hughes | 210/758 |

FOREIGN PATENT DOCUMENTS

| | | |
|---|---|---|
| EP | 116 825 | 8/1984 |
| EP | 253 653 | 1/1989 |
| EP | 427 858 | 5/1991 |
| FR | 1499358 | 12/1996 |
| FR | 2 764 518 | 6/1997 |
| GB | 415213 | 8/1934 |
| GB | 1382820 | 12/1971 |
| JP | 01-046465 | 2/1989 |
| JP | 63-088007 | 4/1989 |
| JP | 01-246204 | 10/1989 |
| JP | 02-161954 | 6/1990 |
| JP | 03-113011 | 5/1991 |
| WO | WO 94/15463 | 7/1994 |
| WO | WO 98/06508 | 2/1998 |
| WO | WO 98/06508 A1 | 2/1998 |
| WO | WO 98/06509 | 2/1998 |
| WO | WO 98/06509 A1 | 2/1998 |
| WO | WO 00/75415 A1 | 12/2000 |
| WO | WO 01/74166 A1 | 10/2001 |
| WO | WO 01/81671 A2 | 11/2001 |

OTHER PUBLICATIONS

Marino, A. et al., "Electrochemical Properties of Silver-Nylon Fabrics," J. Electrochem. Soc. (1985) vol. 132, No. 1, pp. 68-72.

* cited by examiner

METHOD AND DEVICE FOR INACTIVATING VIRUSES

The present specification is a continuation in part from U.S. Ser. No. 10/133,691, filed Apr. 24, 2002, now abandoned.

The present invention relates to a method and a device for inactivating viruses.

More particularly, the present invention relates to a device for the inactivating of viruses utilizing a filter which deactivates the same and to methods for using said filter in various applications including filtering blood donations for blood banks and filtering milk from women infected with HIV for nursing infants without transmission of HIV and in gas masks.

More specifically, according to the present invention there is now provided a device for the inactivation of viruses including HIV, said device comprising a housing delimiting a fluid passageway, said passageway being provided with a filtering material having ionic copper selected from the group consisting of $Cu^+$ and $Cu^{++}$ ions and combinations thereof incorporated therein.

As will be described hereinafter, the term "fluid" as used herein is intended to denote both liquids and especially body fluids, as well as air to be filtered.

The present invention also provides a method for the inactivation of viruses found in cells in body fluids, comprising passing said body fluids through a device for the inactivation of viruses comprising a filtering material, said device having ionic copper selected from the group consisting of $Cu^+$ and $Cu^{++}$ ions and combinations thereof incorporated therein.

In both WO 98/06508 and WO 98/06509 there are taught various aspects of a textile with a full or partial metal or metal oxide plating directly and securely bonded to the fibers thereof, wherein metal and metal oxides, including copper, are bonded to said fibers.

More specifically, in WO 98/06509 there is provided a process comprising the steps of: (a) providing a metallized textile, the metallized textile comprising: (i) a textile including fibers selected from the group consisting of natural fibers, synthetic cellulosic fibers, regenerated fibers, acrylic fibers, polyolefin fibers, polyurethane fibers, vinyl fibers, and blends thereof, and (ii) a plating including materials selected from the group consisting of metals and metal oxides, the metallized textile characterized in that the plating is bonded directly to the fibers; and (b) incorporating the metallized textile in an article of manufacture.

In the context of said invention the term "textile" includes fibers, whether natural (for example, cotton, silk, wool, and linen) or synthetic yarns spun from those fibers, and woven, knit, and non-woven fabrics made of those yarns. The scope of said invention includes all natural fibers; and all synthetic fibers used in textile applications, including but not limited to synthetic cellulosic fibers (i.e., regenerated cellulose fibers such as rayon, and cellulose derivative fibers such as acetate fibers), regenerated protein fibers, acrylic fibers, polyolefin fibers, polyurethane fibers, and vinyl fibers, but excluding nylon and polyester fibers, and blends thereof.

Said invention comprised application to the products of an adaptation of technology used in the electrolyses plating of plastics, particularly printed circuit boards made of plastic, with metals. See, for example, Encyclopedia of Polymer Science and Engineering (Jacqueline I. Kroschwitz, editor), Wiley and Sons, 1987, vol. IX, pp 580-598. As applied to textiles, this process included two steps. The first step was the activation of the textile by precipitating catalytic noble metal nucleation sites on the textile. This was done by first soaking the textile in a solution of a low-oxidation-state reductant cation, and then soaking the textile in a solution of noble metal cations, preferably a solution of Pd++ cations, most preferably an acidic $PdCl_2$ solution. The low-oxidation-state cation reduces the noble metal cations to the noble metals themselves, while being oxidized to a higher oxidation state. Preferably, the reductant cation is one that is soluble in both the initial low oxidation state and the final high oxidation state, for example Sn++, which is oxidized to Sn++++, or Ti+++, which is oxidized to Ti++++.

The second step was the reduction, in close proximity to the activated textile, of a metal cation whose reduction was catalyzed by a noble metal. The reducing agents used to reduce the cations typically were molecular species, for example, formaldehyde in the case of Cu++. Because the reducing agents were oxidized, the metal cations are termed "oxidant cations" herein. The metallized textiles thus produced were characterized in that their metal plating was bonded directly to the textile fibers.

In WO 98/06508 there is described and claimed a composition of matter comprising:
(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and
(b) a plating including materials selected from the group consisting of metals and metal oxides;

the composition of matter characterized in that said plating is bonded directly to said fibers.

Said publication also claims a composition of matter comprising:
(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and
(b) a plurality of nucleation sites, each of said nucleation sites including at least one noble metal;

the composition of matter characterized by catalyzing the reduction of at least one metallic cationic species to a reduced metal, thereby plating said fibers with said reduced metal.

In addition, said publication teaches and claims processes for producing said products.

A preferred process for preparing a metallized textile according to said publication comprises the steps of:
a) selecting a textile, in a form selected from the group consisting of yarn and fabric, said textile including fibers selected from the group consisting of natural fibers, synthetic cellulosic fibers, regenerated protein fibers, acrylic fibers, polyolefin fibers, polyurethane fibers, vinyl fibers, and blends thereof;
b) soaking said textile in a solution containing at least one reductant cationic species having at least two positive oxidation states, said at least one cationic species being in a lower of said at least two positive oxidation states;
c) soaking said textile in a solution containing at least one noble metal cationic species, thereby producing an activated textile; and
d) reducing at least one oxidant cationic species in a medium in contact with said activated textile, thereby producing a metallized textile.

While the metallized fabrics produced according to said publications are effective acaricides, it was found that they are also effective in preventing and/or treating bacterial, fungal and yeast infections which afflict various parts of the human body and that therefore the incorporation of at least a panel of a metallized textile material in an article of clothing can have extremely beneficial effect.

Thus, in U.S. Pat. No. 6,124,221 there is described and claimed an article of clothing having antibacterial, antifungal, and antiyeast properties, comprising at least a panel of a metallized textile, the textile including fibers selected from the group consisting of natural fibers, synthetic cellulosic fibers, regenerated protein fibers, acrylic fibers, polyolefin fibers, polyurethane fibers, vinyl fibers, and blends thereof, and having a plating including an antibacterial, antifungal and antiyeast effective amount of at least one oxidant cationic species of copper.

In said specification there was described that said article of clothing was effective against *Tinea Pedis*, against *Candida Albicans*, against Thrush and against bacteria causing foot odor, selected from the group of brevubacterium, *acinetobacter, micrococcus* and combinations thereof.

Thus, said invention was especially designed for preparation of articles such as underwear and articles of hosiery.

In WO 01/81671 there is described that textile fabrics incorporating fibers coated with a cationic form of copper are also effective for the inactivation of antibiotic resistant strains of bacteria and said cationic species of copper preferably comprises $Cu^{++}$ ions.

Already in July of 1991 Anders R. Karlstrom et al., published findings that copper inhibits the protease from HIV 1 virus in Proc. Natl. Acad. Sci. USA, Vol. 88, pp. 5552-5556.

Similarly, in 1993 A. R. Karlstrom et al. published further findings relating to the inactivation of HIV-1 protease using copper in Arch. Biochem Biophys. 304:163-169.

In addition, in 1996 Jose-Luis Sagripanti et al., published findings that Cupric and Ferric Ions inactivate HIV in Aids Research and Human Retroviruses, Vol. 12, Number 4, 1996.

Despite said publications, the first of which was over a decade ago, heretofore it has not been obvious and no one has suggested the use of cupric ions for the solution of at least two major HIV problems which are plaguing the world.

The first of these problems is that in that in the third world countries and especially in African countries entire populations are being decimated by HIV due to the transmission of HIV from infected mothers to their newborn babies via nursing milk.

Due to the poverty prevalent in these countries milk substitutes are not available to newborn and nursing babies and infected mother's milk has been found to be the major cause of transmission of HIV to children. When milk substitutes have been made available there is still the problem of parasites in the water which make the use of these substitutes counter productive.

A further acute problem which also exists in the Western world is the fear of transfusion of HIV and other pathogenic viruses in contaminated blood.

While blood banks now screen donated blood for HIV antibodies it is known that the test for antibodies is only effective after the incubation period of 60-90 days and therefore there is always the danger that this screening process will not detect the blood of an individual who only contracted HIV within 2 or 3 months of the donation. In addition, there are patogenic viruses which have been shown to be contained in transfused blood for which no system of detection eixts. A case in point, at the time of the writing of this document, is the West Nile Fever virus. It is now known that one can be a carrier of the disease and not be ill with the disease. The virus has been transmitted to blood and organ receipitants which, in some cases, caused patient mortality.

In WO 01/74166 there is described and claimed the use of particles which release $Cu^{++}$ for the preparation of a polymeric material having microscopic particles which release $Cu^{++}$ encapsulated therein with a portion of said particles being exposed and protruding from surfaces thereof, said polymeric material being effective to inhibit HIV-1 proliferation, however, said publication was limited to the teaching of the use of such polymeric materials for the preparation of condoms and possibly gloves and the inventor thereof did not realize at said time and said publication does not teach or suggest the present inventive concept of providing a device and method for the inactivation of HIV comprising a filtering material, said device having ionic copper selected from the group consisting of $Cu^+$ and $Cu^{++}$ ions and combinations thereof incorporated therein.

Thus, none of the above publications teach or suggest the subject matter of the present invention.

It will be realized that the device and method of the present invention is not limited to the above mentioned preferred uses and that the device can also be used in a hospital or field hospital setting wherein blood from a blood bank is not available and a direct transfusion is mandated.

Furthermore, the device of the present invention can be used beneficially in a manner wherein blood is drawn from a person infected with HIV passed through the device in a similar manner to the use of a dialysis machine and then returned to the patient.

In further embodiments of the present invention the device of the present invention can also be used to inactivate other viruses found in body fluids including the inactivation of West Nile fever which has now been discovered to exist in the blood of carriers of said disease who do not show symptoms thereof however whose blood could contaminate blood banks by transmission of said virus thereto.

Thus it has now been discovered that the device of the present invention has general antiviral properties as demonstrated hereinafter in its ability to inactivate HIV virus, Andenovirus, which is a double stranted DNA virus and to inactivate West Nile fever virus.

Adenovirus infections occur worldwide in humans as well as in a variety of animals. Adenoviruses can commonly infect and replicate at various sites of the respiratory tract as well as in the eye and gastrointestinal tract. Several diseases cn be causes by adenviruses, such as: acute febril pharyngitis, acute respiratory disease, pneumonia, epidemic keratoconjunctivities, pertussis-like syndrome, gasroenteritis, hepatitis and myocarditis.

In the device and method of the present invention the cationic species of copper must be exposed to the liquid medium being filtered to allow for atomic dispersion into the medium. To achieve this, the exposure can be accomplished in a number of ways:

a) A copper species in powder or fiber form can be placed in an envelope made from two filtration layers and sealed to prevent escape into the medium;
b) A copper species in powder or fiber form can be added to a membrane while still in a slurry state;
c) Copper plated fibers can be placed loosely between two layers in the filter;
d) The membrane substrate can be plated with a cationic copper species; or
e) A porous polymer can be utilized as the substrate for the filter and the copper is added as a dust in slurry form and encapsulated within said porous polymer.

As will be realized adenoviruses include viruses which are among those feared for use in "bacterial warfare".

Therefore, in further embodiments of the present invention there is provided a device for inactivating airborn epidemeal viruses, said device having ionic copper selected from the group consisting of $Cu^+$ and $Cu^{++}$ ions and combinations thereof incorporated therein, wherein said ionic copper is attached to fibers incorporated in a layer in said device wherein said device is a gas mask.

The manufacture of gas masks for protection against chemical and bacterial warfare is known per se and need not be described.

In order to incorporate a filter of the present invention in a gas mask one would take fibers having ionic copper selected from the group consisting of $Cu^+$ and $Cu^{++}$ ions and include them in a substrate. In a woven substrate, the fibers would be blended with any other fiber and woven or knit into a substrate. In a non-woven configuration the fibers would be blended to form a thin layer. In both cases, a number of layers would be placed one on top of the other to form a pad which would be added to the breathing filter of the gas mask. Since the pad is highly permeable, breathing would not be restricted. The moisture of the breath of the wearer would be enough to activate the ionic release and effect the deactivation of the virus.

The amount of copper coated fibers necessary would vary with the thickness of the pad being included in the mask. Basically, there has to be enough fiber to cover 100% of the area of the pad which can be done over any number of layers.

In the embodiments used for the experiments described hereinafter, the material containing and adapted to release ionic copper, was prepared as follows:

The ionic copper used in the device of the present invention is prepared in a manner similar to that described in the earlier specifications referenced above with slight modifications as described hereinafter and is obtained through a redox reaction either on a substrate or alone in the liquid. The method of production is an adaptation of technology as used in the electroless plating of plastics, particularly printed circuit boards made of plastic, with metals. See, for example, Encyclopedia of Polymer Science and Engineering (Jacqueline I. Kroschwitz, editor), Wiley and Sons, 1987, vol. IX, pp 580-598. As applied to fibers or fabrics or membranes, this process includes two steps. The first step is the activation of the substrate by precipitating a catalytic noble metal nucleation sites on the substrate suface. This is done by first soaking the substrate in a solution of a low-oxidation-state reductant cation, and then soaking the substrate in a solution of noble metals cations, preferably a solution of Pd++ cations, most preferable an acidic PdCl2 solution. The low-oxidation-state cation reduces the noble metal cations to the noble metals themselves, while being oxidized to a higher oxidation state. Preferable, the reductant cation is one that is soluble in both the initial low oxidation state and the final high oxidation state, for example Sn++, which is oxidized to Sn++++, or Ti+++. Which is oxidized to Ti++++.

The second step is the reduction, in close proximity to the activated substrate, of a metal cation whose reduction is catalyzed by a noble metal. The reducing agents used to reduce the cations typically are molecular species, for example, formaldehyde in the case of Cu++. Because the reducing agents is oxidized, the metal cations are termed "oxidant cations" herein. The metallized substrate thus produced is characterized in that their metal plating is bonded directly to the substrate.

Based on the process described above, it is also possible for someone familiar with the art to identify the oxidant states by their colors. When the substrate is allowed to float in a copper solution for reduction as described above, different colors are obtained on each side of the substrate. The topside of the substrate is the shiny bright copper (red/yellow) color characteristic of elemental copper—Cu. The bottom side of the fabric is a black color, which is characteristic of CuO. Any substrate located under the top substrate also shows a black shade on its upper side.

In the process described herein, changes are made to the process to allow the plating of a cellulose fiber or substrate with a different cationic species of copper than elemental copper or copper oxide (CuO—black).

This form of electro-less plating process involves the reduction of a cationic form of copper from a copper solution such as copper sulfate or copper nitrate on to a prepared surface on fibers or a substrate. The fibers or substrate to be plated must first be soaked in a solution containing at least one reductant cationic species having at least two positive oxidation states, then at least one cationic species being in a lower of the at least two positive oxidation states. The fibers or substrate are then soaked in a solution containing at least one noble metal cationic species, thereby producing an activated surface.

The fibers are then exposed to at least one oxidant cationic species in a medium in contact with the activated surface. A reducing agent is then added and the copper reduces itself from the solution on to the surface of the fibers. Without the following changes, the fibers or substrate produced using this formula demonstrates an elemental copper coating on the fibers which are on the top of the fiber or substrate pack and black colored fibers below and throughout the fiber or substrate pack.

As stated hereinbefore, in order to obtain a surface that is effective for the inactivation of HIV a cationic species of copper must be obtained. The effective compounds of copper must contain either a Cu (I) or Cu (II) species or both. To insure obtaining these species on cellulose, the Pd++ must be applied so that there is equal saturation of all fibers at the same time. If a large fiber pack is dropped into the Pd++ solution, the first fibers to hit the solution will absorb more of the Pd++ solution than other parts of the pack, which will upset the cationic copper deposition. In addition, the fibers must be washed between the first process involving the Sn++ and the second process, Pd++, in water. Residual Sn++ solution left between the fibers will cause a reduction of the Pd++ directly into the solution between the fibers and will allow only a random reduction of the Pd++ on the fibers which will again effect the deposition of the copper. While these two points may seem small, they have a direct effect on the plating.

In addition, a change is necessary in the application system of the copper solution to the process. A side effect of the reduction process on to the fibers is the creation of hydrogen. This hydrogen appears as bubbles on the surface of the fibers. The hydrogen forms as a result of the interaction in the copper solution with the Pd++ on the fiber surface. If the hydrogen is not removed from the surface of the fibers immediately upon their formation, the fibers exposed to the air will be coated with an elemental copper. The fibers just below the surface of the elemental copper will be black copper oxide. If, however, the hydrogen is removed immediately with their formation of the bubbles, the desired cationic species is obtained throughout the fiber pack. The desired color will be a dark brown which is distinct from the copper metal color or the black copper oxide. A further indication of the cationic species is that the fibers will not conduct electricity.

This process yields both a Cu (I) and a Cu (II) species as part of a copper oxide molecule. Analysis has shown that formed on the surface in the $Cu_2O$ is 70% Cu (I), 30% Cu (II). These compounds have been proven to be a highly effective in the inactivation of HIV. The antiviral activity takes advantage of the redox reaction of the cationic species with water and allows a switch between Cu (II) and Cu (I) when there is contact with water. Cu(I) is more effective than Cu(II) against HIV while Cu(II) is more stable than Cu(I). The Cu(II) compound will oxidize much more slowly than the Cu(I) compound and will increase the shelf life of the product.

While the invention will now be described in connection with certain preferred embodiments in the following examples and with reference to the attached figures, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Figure 1:
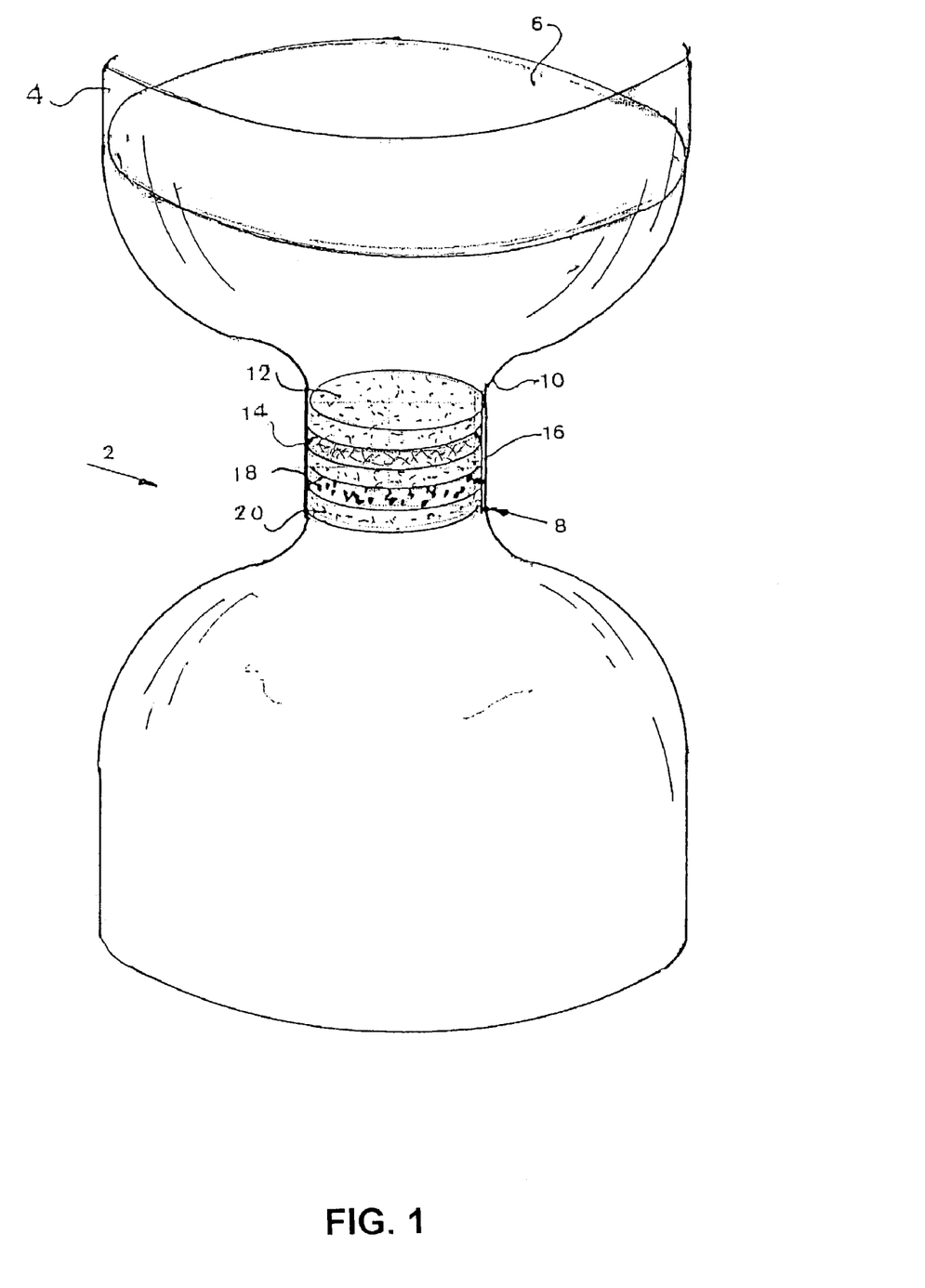
FIG. 1 is a schematic representation of a device according to the present invention.

Referring to FIG. 1 there is seen a schematic representation of a device 2 according to the present invention having a container 4 for receiving unfiltered liquid medium 6 which can be blood or mothers milk and leading to a filter unit 8 provided at the outlet 10 thereof said unit comprising a first porous medium 12 at the inlet of said unit 8 followed by a material 14 containing and adapted to release ionic copper selected from the group consisting of $Cu^+$ and $Cu^{++}$ ions and combinations thereof wherein said ionic copper has been introduced into said material after being prepared as described above.

Said layer of material 14 is optionally followed by a further layer incorporating a filter 16 of up to 0.6 microns for removal of white blood cells from the fluid passing therethrough.

Following layer 14 or optionally layer 16 there is found a layer 18 of activated charcoal for removal of copper ions from the fluid passing through the filter which layer is followed by a further filter 20 for removal of residual charcoal particles, which filter 20 preferably prevents the passage of particles greater than 0.4 microns.

The device will further be provided with pumping means, not shown, for facilitating the transfer of the liquid through the filtering device 2.

As will be realized, the above description relates to FIG. 1 which is merely a schematic representation of a possible device for use in blood banks and similar uses and the device for distribution to infected nursing mothers will probably be a breast pump designed to extract milk from a mother's breast and then pump the same through a filter device according the present invention.

Figure 2:
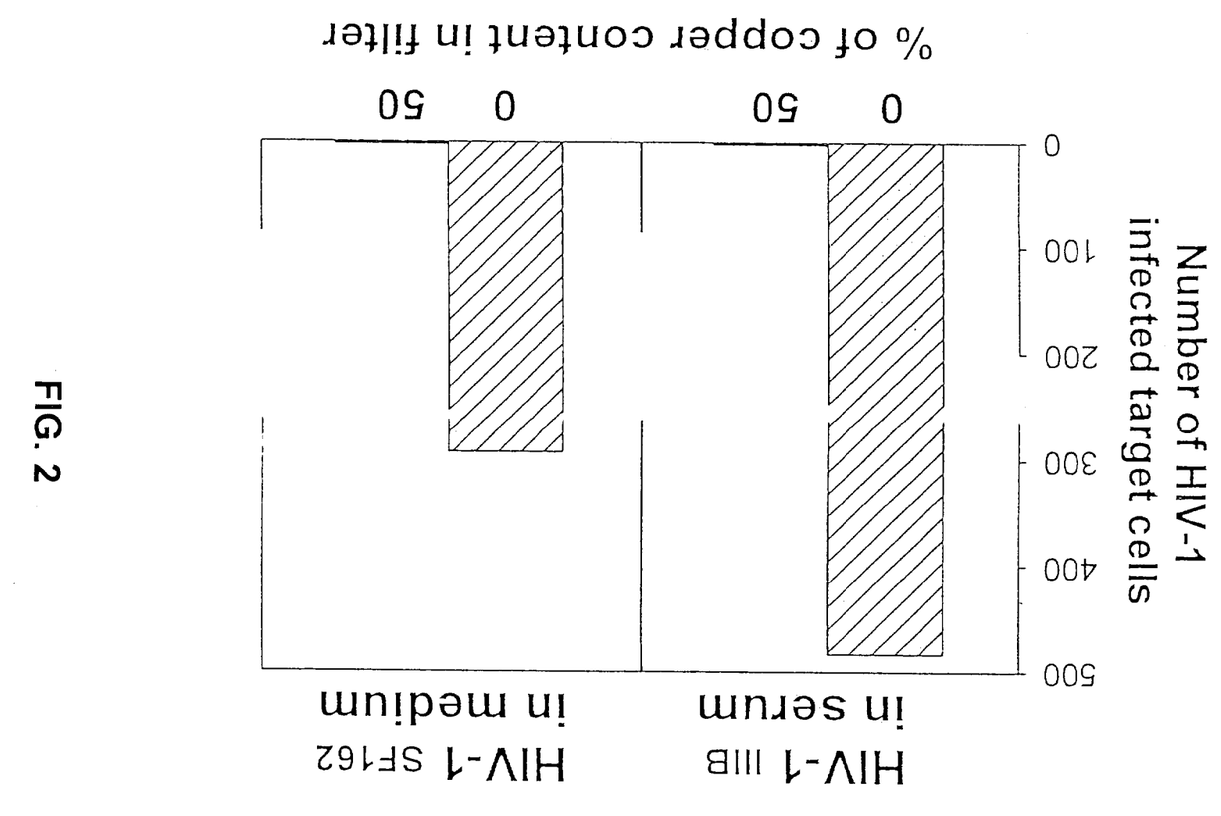
FIG. 2 is a graph showing the inactivation of HIV-1 in serum and in medium utilizing $Cu^{++}$.
Figure 3:
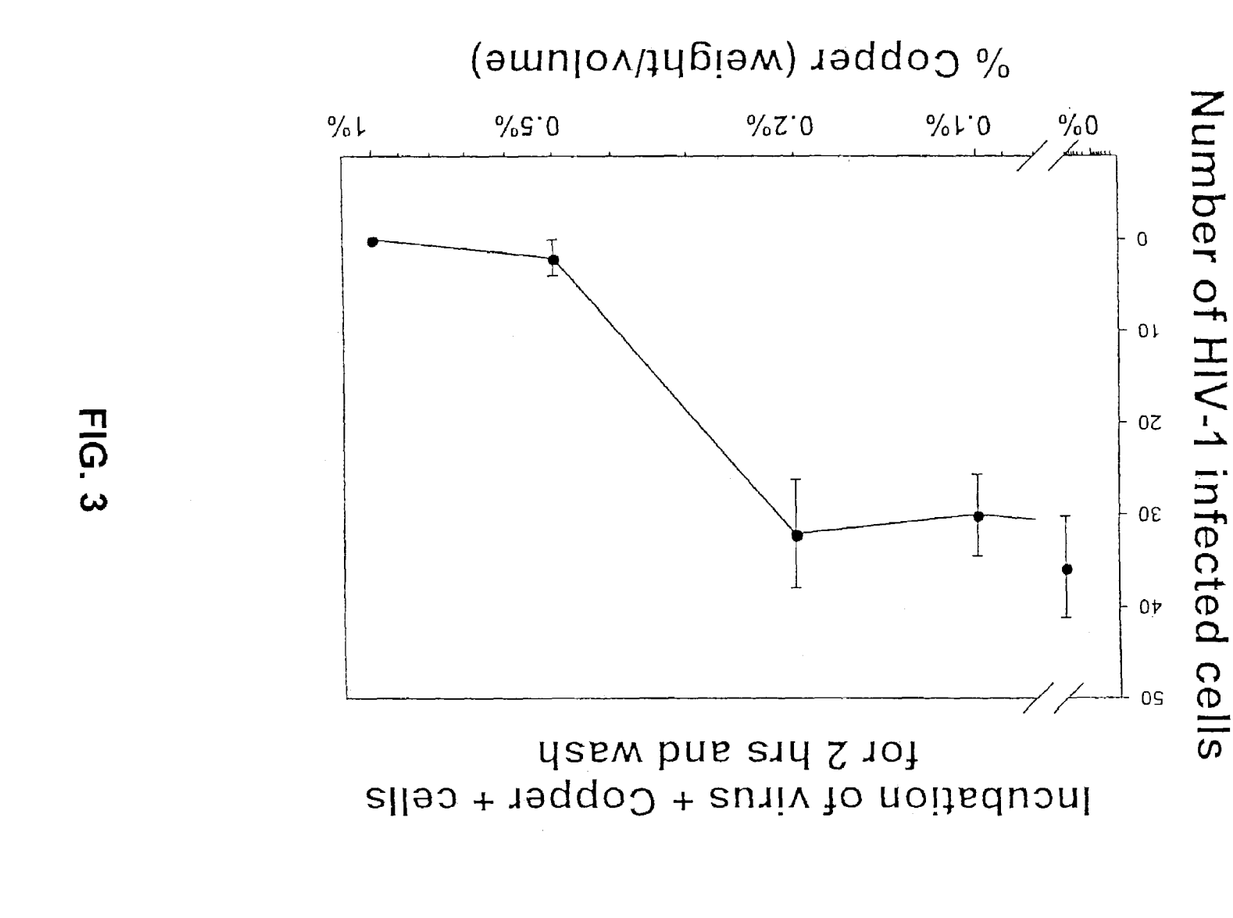
FIG. 3 is a graph showing a dose response inactivation of HIV-1 by $Cu^{++}$.
Figure 4:
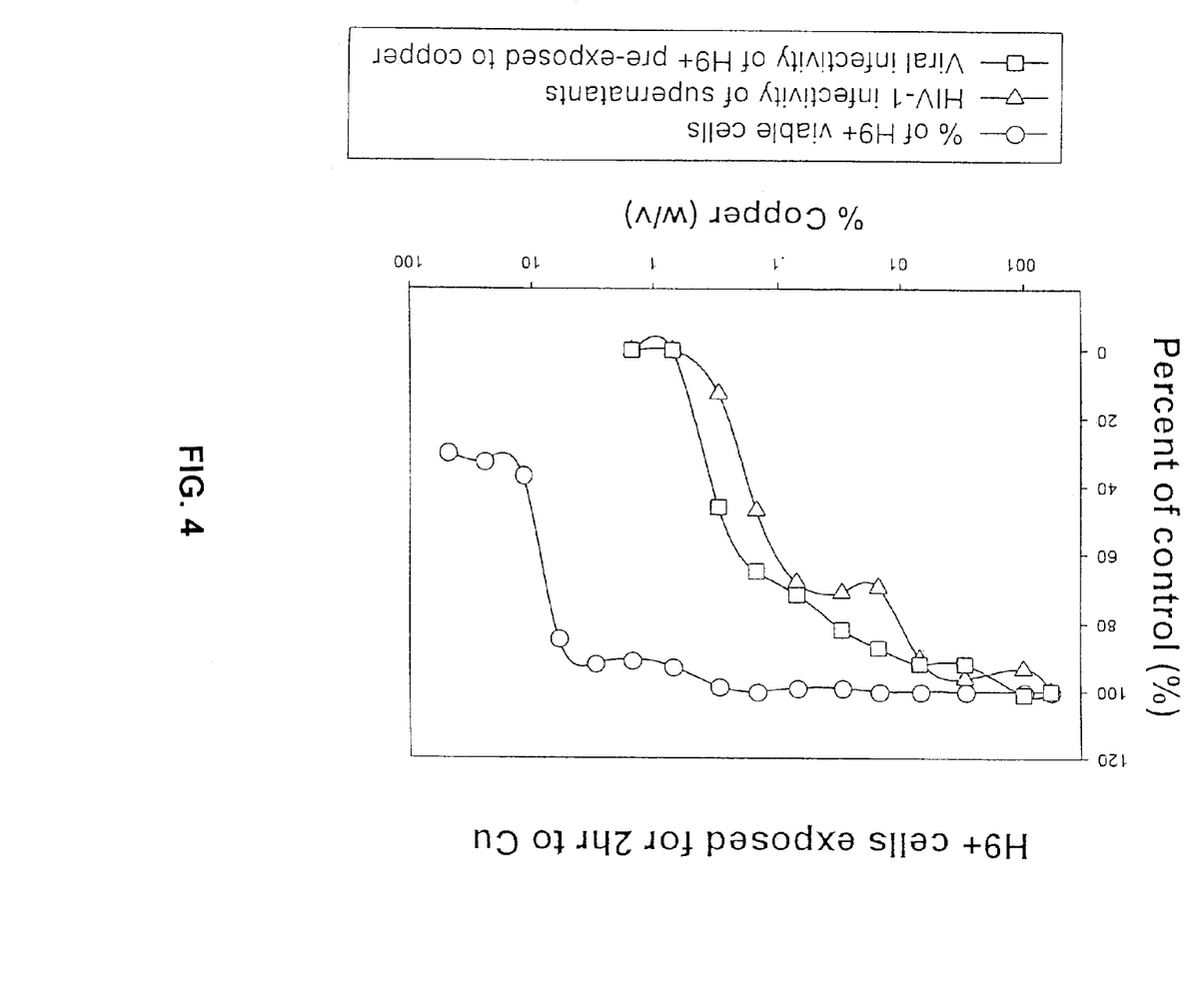
FIG. 4 is a graph showing the inactivation of HIV-1 cell-associated transmission as well as cytotoxicity of medium treated with different concentrations of $Cu^{++}$.

The efficacy of the present invention to neutralize cell-free HIV-1 infectivity will now be demonstrated with reference to FIGS. 2, 3 and 4, which are graphical representations of the following experiments carried out independently by Dr. Gadi Borkow, Senior Scientist at the Ruth Ben-Ari Institute of Clinical Immunology and AIDS Center at Kaplan Medical Center, Rechovot, Israel.

EXAMPLE 1

Human plasma or RPMI 1640 medium (GibcoBRL, Life Technologies, Paisley, UK) containing $10^6 \times TCID_{50}$ (Tissue Culture InDose that causes in 50% of the cases infection) of either one of the following syncytia inducing (T cell tropic) wild type laboratory or primary clinical HIV-1 isolates from clades A, B, or C, or nucleoside, non-nucleoside or protease resistant lade B HIV-1 isolates, or non-syncytia inducing (Macrophage tropic) lade B HIV-1 isolate, were added to shafts containing different concentrations of copper powder (expressed as a percentage of copper weight per volume of medium). After 5 minutes of incubation the medium was passed through a 0.2 μm syringe filter (Sartorius, Gottingen, Germany) and through another shaft containing 100 mg of carbon (activated charcoal). Then aliquots (10, 20 and 50 μl) of the filtrate were added to $10^5$ target cells, either cMAGI (a T-cell line in which the cells grow as a monolayer attached to the bottom of the wells) or MT-2 cells (T-cell line in which the cells grow as suspension), which were cultured for 3 days at 37° C. in a 5% $CO_2$ moist incubator. As control the virus was passed under the same conditions through filters without copper.

Viral infectivity was determined by measuring HIV-1 p24 antigen levels (p24 antigen capture kit, SAIC Frederick, Frederick, Md., USA, according to the manufacturers instructions), and/or by counting HIV-1 infected cMAGI indicator cells (the cells, which are stably transfected with a plasmid containing the HIV-1 LTR fused to β-galactosidase gene, are stained blue when infected with HIV-1). Cytopathic effects of HIV-1 infection of MT2 cells were also analyzed by microscopic assessment of syncytium formation. The latter data were obtained by analysis of duplicate samples by two independent observers.

As shown in two representative examples in FIG. 2, the infectivity of HIV-$1_{IIIB}$ or HIV-1 SF162 in serum or medium, respectively, after being filtered through a 50% copper filter was abolished, as determined by the number of cMAGI cells that were blue (i.e. cells that are infected with HIV-1 are stained blue), in contrast to the same amount of virus that was filtered through the same filters but without copper (0%), which resulted in high infectivity.

Similar results were obtained by all other above mentioned HIV-1 isolates, showing the capacity of the Copper filters to abolish the infectivity of a wide range of HIV-1 isolates, including primary clinical isolates and isolates resistant to currently clinically used antivirals. Furthermore, HIV-1 infectivity was abolished when the virus was exposed for 5 minutes even to only 10% (weight/volume) copper filters.

As shown in FIG. 3, significantly lower amounts of copper are needed if the virus is exposed for longer periods of time to copper. The experiment was carried out as follows: 1 ml of RPMI medium only or RPMI medium containing 0.1%, 0.2%, 0.5% or 1% of copper (weight/volume) was added to cMAGI cells. Immediately afterwards $10^6$ $TCID_{50}$ HIV-1$_{IIIB}$ were added to each well. After 2 hr of incubation in a moist incubator at 37° C., the mixtures and virus were removed thoroughly and fresh RPMI medium, containing 10% fetal calf serum and antibiotics, was added to the wells. The cells were then cultured for 3 days at 37° C. in a moist incubator, and then the number of HIV-1 infected cells (blue cells) was determined.

EXAMPLE 2

The efficacy of the present invention to neutralize cell-associated HIV-1 infectivity will now be demonstrated with reference to FIG. 4.

For the tests shown in FIG. 4 an H9+ cell line was used. This cell line was used because the cells are chronically infected with HIV-1 III$_B$ and constantly produce and secrete HIV-1 virions into the RPMI medium in which they are located.

100,000 H9+ washed cells, were resuspended in media, previously exposed to different concentrations of copper powder. After 3 hr of incubation at 37° C. in a moist incubator, the cells were pelleted by centrifugation. Ten μl aliquots of the supernatants, containing the HIV virions that budded out during the period of exposure to the copper, were added to target non-infected cMAGI cells. After 3 days of incubation the number of infected target cMAGI was determined, and the results are presented as a percentage of infectivity of each supernatant in comparison to the infectivity of the supernatant from H9+ cells not exposed to copper (FIG. 4, triangular dots).

In addition, the pelleted H9+ cells were resuspended with fresh media and the pre-treated H9+ cells were co-cultured with attached cMAGI target cells (10,000 H9+ cells per well), allowing for cell-associated HIV-1 transmission to occur. After 2 hr of incubation the suspended H9+ cells were removed from the cMAGI monolayer and discarded. The cMAGI target cells were cultured for three days and the amount of cells infected with HIV-1 was then determined (FIG. 4, square dots). This part of the experiment analyzed the effect of the exposure of the chronically infected cells H9+ to the copper, on the progeny virus (subsequent newly budded virions).

In parallel, the viability (expressed as percent of control untreated cells) of the H9+ cells exposed to the various copper concentrations is also shown in FIG. 4 (round dots). The viability of the cells was determined by a tetrazolium-based colorimetric assay (MTT assay) using a cell proliferation kit (CellTiter 96® Aq$_{ueous}$ One solution Cell Proliferation Assay, Promega, Wis., USA), and by trypan blue exclusion assay.

EXAMPLE 3

West Nile Fever

Six filters according to the present invention as described hereinbefore were prepared.

1. $10^{5.83}$ $TCID_{50}$/50 μl West Nile Virus (WNV) field strain was filtered through 6 filters.
2. The filtered virus was diluted tenfold ($10^{-1}$-$10^{-6}$) and 50 μl aliquots were added to Vero monolayers cells. Each sample was added to six different wells.
3. After 6-7 days of incubation at 37° C. the cytophatic effect (cell death) was determined for each filtrate.
4. As positive control unfiltered virus was titrated in parallel dilutions.

Figure 5:
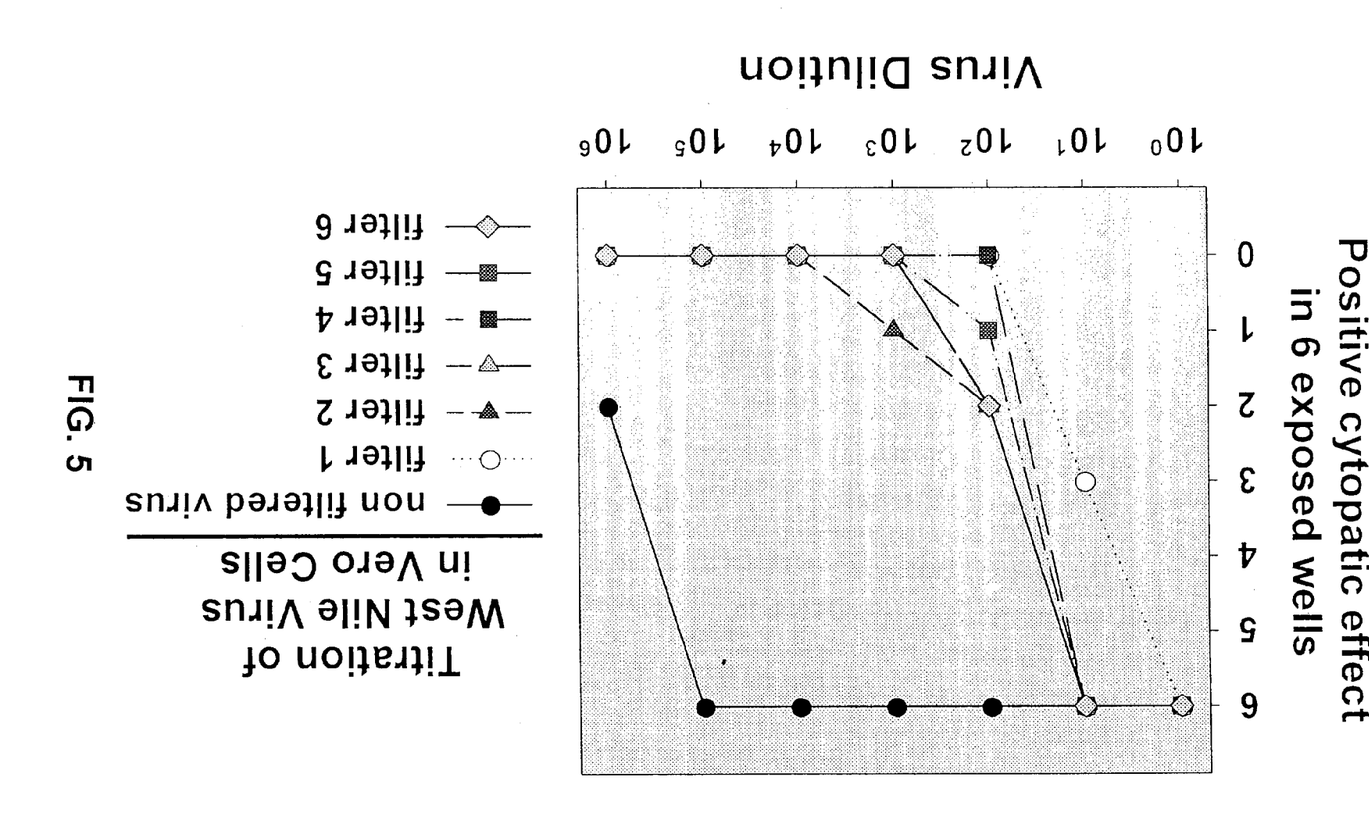
FIG. 5 is a graph showing the inactivation of West Nile fever virus.

The results are described in the attached FIG. 5. Basically there is at least 4 orders of magnitude of inhibition of the cytophatic effect of the filtered virus.

EXAMPLE 4

A retrovirus designated Ad-HIVluc (this recombinant adenovirus contains an HIV-1 dependant luciferase gene, therefore serving as a reporter vector for HIV-1 infection; Axelrod and Honigman, AIDS Research and Human Retroviruses, 1999, 15:759-767) was tested for its cytopathogenic effect after its passage through the filters of the present invention in two separate experiments. As control there was used the same virus but without passing it through the filter.

The results of both experiments are hereby described:

EXAMPLE 4a

Adenoviral stocks were diluted 1:10 in cell culture medium and passed through the a filter according to the present invention.

10, 20, 50 and 100 μl of the filtrate were added to 293 cells (human kidney cells) and the cells were examined daily by a microscope. After 5 days of culture two independent observers estimated the cytophatic effects. The following Table shows the estimated % of cytopathicity.

|  | 100 | 50 | 20 | 10 | 0 | (μl added/well) |
|---|---|---|---|---|---|---|
| Adenovirus not filtered: | 80 | 65 | 50 | 40 | 0 | (% cytopathicity) |
| Adenovirus filtered: | 5 | 0 | 0 | 0 | 0 | (% cytopathicity) |

EXAMPLE 4b

Adenoviral stocks in cell culture medium were passed through filters according to the present invention and added to cMAGI cells previously infected with HIV-1 (final dilution of the adnovirus 1:10). After overnight incubation the cells were lysed and the amount of HIV-1 luciferase activity was measured. The amount of light emitted by the HIV-1 cells superinfected with the adenovirus that was passed through the filters was 75±34 relative light units, while that emitted by the HIV-1 infected cells superinfected by the control non-filtered adenovirus was 4085±758 relative light units, being the inhibition of adenovirus replication ~98%.

Figure 6:
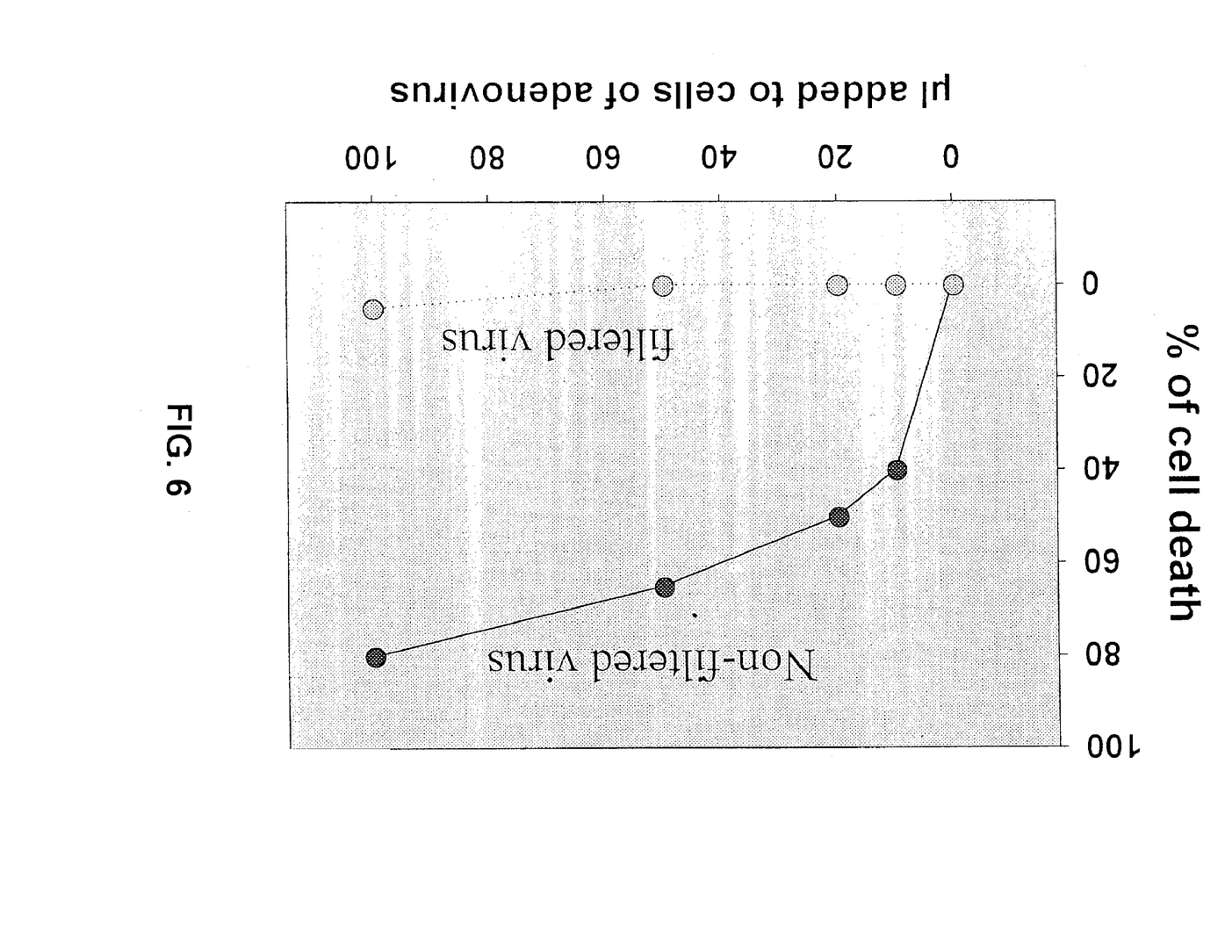
FIG. 6 is a graph showing the neutralization of adenovirus.
Figure 7:
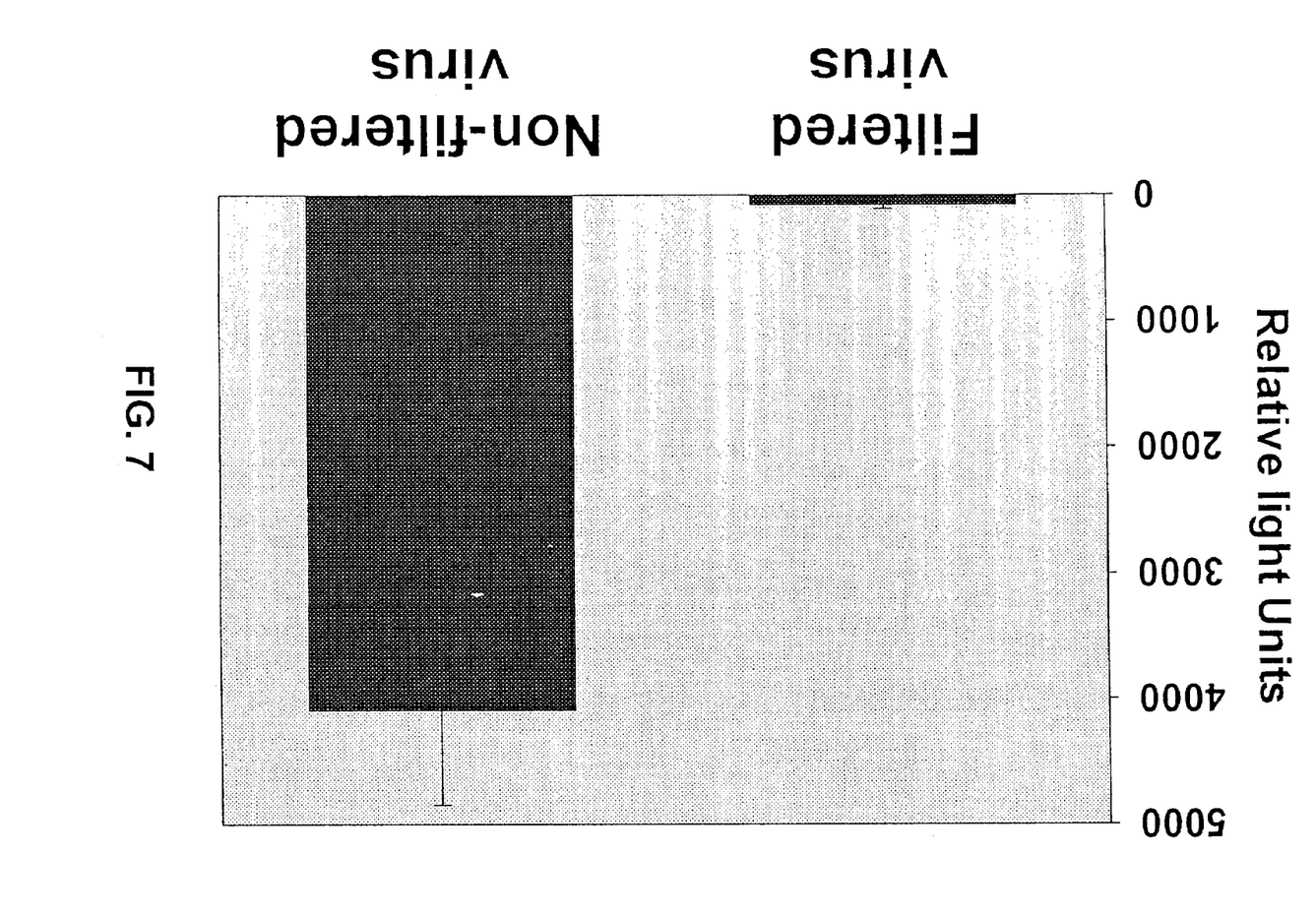
FIG. 7 is a tabular representation of the neutralization of adenovirus.

The results of these experiments are shown graphically in FIGS. 6 and 7 appended hereto.

It will be evident to those skilled in the art that the invention is not limited to the details of the foregoing illustrative examples and figures and that the present invention may be embodied in other specific for without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A device for the inactivation of a virus comprising: a housing delimiting a fluid passageway, said passageway being provided with a virus-inactivating fibrous material, said virus-inactivating fibrous material comprising a plurality of fibers having incorporated therein a single antiviral component consisting essentially of a water-insoluble form of opper oxide molecules which release both $Cu^+$ and $Cu^{++}$ ions, wherein the copper oxide molecules are directly attached to the fibers in said material by an electro-less plating process involving reduction of cationic copper from a copper solution, and wherein the ionic copper is exposed to fluid in the passageway to allow for atomic dispersion of the ionic copper into the fluid, whereby the ionic copper can inactivate a virus present in the fluid.

2. A device according to claim 1 comprising a multi-layered filter having a first porous medium at the inlet thereof, followed by a material containing said copper oxide molecules, followed by a layer of activated charcoal for removal of copper ions, followed by a filtering material for removal of residual charcoal particles.

3. A device according to claim 2 further comprising a pump that facilitates transfer of a media through the device.

4. A device according to claim 2 further comprising a filter of up to 0.6 microns for removal of white blood cells from the fluid passing therethrough.

5. A device according to claim 2 wherein said filtering material for removal of said charcoal particles prevents the passage of particles greater than 0.4 microns.

6. A device according to claim 1 wherein said device is a gas mask.

7. A device according to claim 6 wherein said virus is an airborne virus and said copper oxide molecules which release both $Cu^+$ and $Cu^{++}$ ions are directly attached to fibers incorporated into a non-woven fabric.

8. A method for inactivating a virus found in a body fluid, comprising:
passing said body fluids through a device as defined in claim 1 wherein live virus in the body fluid is inactivated after passing through the device.

9. A method according to claim 8 wherein said virus is HIV.

10. A method according to claim 8 wherein said body fluid is blood.

11. A method according to claim 8 wherein said body fluid is milk.

12. A method according to claim 8 wherein said body fluid is blood which is then returned to the body from which it has been drawn.

13. A method according to claim 8 wherein said virus is West Nile Fever Virus.

14. A device for inactivating airborne epidemial viruses, said device being provided with a virus-inactivating fibrous material, said virus-inactivating fibrous material comprising a plurality of fibers having incorporated therein a single antiviral component consisting essentially of a water-insoluble form of copper oxide molecules which release both $Cu^+$ and $Cu^{++}$ ions, wherein the copper oxide molecules are directly attached to fibers by an electro-less plating process involving reduction of cationic copper from a copper solution, wherein said fibers are incorporated in a layer in said device and wherein said device is a gas mask.

15. A device according to claim 14 wherein said virus is an airborne virus and said copper oxide molecules which release both $Cu^+$ and $Cu^{++}$ ions are directly attached to fibers incorporated into a non-woven fabric.

* * * * *

UNITED STATES PATENT AND TRADEMARK OFFICE
CERTIFICATE OF CORRECTION

| | | |
|---|---|---|
| PATENT NO. | : 7,296,690 B2 | Page 1 of 1 |
| APPLICATION NO. | : 10/339886 | |
| DATED | : November 20, 2007 | |
| INVENTOR(S) | : Jeffrey Gabbay | |

It is certified that error appears in the above-identified patent and that said Letters Patent is hereby corrected as shown below:

Column 11, claim 1, line 7, delete "opper" and insert --copper--

Signed and Sealed this

Twenty-fourth Day of June, 2008

JON W. DUDAS
*Director of the United States Patent and Trademark Office*